United States Patent [19]

Cheung et al.

[11] Patent Number: 5,074,977
[45] Date of Patent: Dec. 24, 1991

[54] DIGITAL BIOSENSORS AND METHOD OF USING SAME

[75] Inventors: Peter W. Cheung, Mercer Island; Edward B. Wieler; Clement E. Furlong, Jr., both of Seattle, all of Wash.

[73] Assignee: The Washington Technology Center, Seattle, Wash.

[21] Appl. No.: 601,940

[22] Filed: Oct. 23, 1990

Related U.S. Application Data

[63] Continuation of Ser. No. 47,080, May 5, 1987, abandoned.

[51] Int. Cl.$^5$ .................................. G01N 27/327
[52] U.S. Cl. .......................... 204/153.1; 204/153.12; 204/400; 204/403; 435/4; 435/7.1; 435/817; 436/518; 436/806
[58] Field of Search .............. 204/153.1, 153.12, 400, 204/403, 416, 418; 435/4, 7, 817; 436/518, 806

[56] References Cited

U.S. PATENT DOCUMENTS

| | | |
|---|---|---|
| 3,831,432 | 8/1974 | Cox . |
| 4,020,830 | 9/1977 | Johnson et al. ............... 128/635 |
| 4,020,830 | 5/1977 | Johnson et al. ............... 128/2 E |
| 4,225,410 | 9/1980 | Pace ............................. 204/195 R |
| 4,238,757 | 12/1980 | Schenck ........................ 436/806 |
| 4,334,880 | 6/1982 | Malmros . |
| 4,388,166 | 6/1983 | Suzuki et al. .................. 204/403 |
| 4,490,216 | 12/1984 | McConnell ..................... 204/1 T |
| 4,562,157 | 12/1985 | Lowe et al. .................... 435/291 |
| 4,571,292 | 2/1986 | Liu et al. ........................ 204/412 |
| 4,591,550 | 5/1986 | Hafeman et al. ................ 435/4 |
| 4,778,769 | 10/1988 | Forrest et al. . |

FOREIGN PATENT DOCUMENTS

| | | |
|---|---|---|
| 96095 | 12/1983 | European Pat. Off. . |
| 155193 | 9/1985 | European Pat. Off. . |
| 214805 | 3/1987 | European Pat. Off. . |
| 2304083 | 8/1976 | France . |
| 60029658 | 7/1983 | Japan . |
| 602518833 | 5/1984 | Japan . |
| 59-125054 | 7/1984 | Japan . |
| WO83/02669 | 4/1983 | PCT Int'l Appl. . |
| WO85/04480 | 10/1985 | PCT Int'l Appl. . |

OTHER PUBLICATIONS

Smith et al., "Principles of Biochemistry: General Aspects", 1983, 7th ed., pp. 57, 389, 390.
Oka, S. et al., "Anion Sensor Fabrication," *Chemical Abstracts*, vol. 106, 1987, p. 718.

(List continued on next page.)

*Attorney, Agent, or Firm*—Christensen, O'Connor, Johnson & Kindness

[57] ABSTRACT

A mearsuring instrument is disclosed having a reversibly selective binding protein immobilized upon the insulated-gate region of a field-effect transistor located on a sensor. With the sensor immersed in solution, the protein binds a select component of the solution to the gate producing an effect on a current flowing through the IGFET. A plurality of such binding protein-IGFET arrangements can be provided on the same sensor, including the same binding proteins having different binding coefficients $K_D$ or an array of proteins with different ligand specificity and/or affinity. Analysis of the IGFET's response to binding by a microprocessor allows, for example, the concentration of the component in solution to be determined. With a plurality of different binding proteins employed, the concentration of different components can be determined. Similarly, with binding proteins employed having different binding coefficients $K_D$, the output of the sensor can be analyzed in either a digital or analog manner, or some combination of the two. To release the component from the protein, heat can be applied to the sensor through a resistive bank integrated into the sensor chip. Alternatively, the application of a reverse bias to the gate can be used to enhance release.

13 Claims, 4 Drawing Sheets

OTHER PUBLICATIONS

Terajima, M. et al., "Ion-Selective Electrode Fabrication," *Chemical Abstracts*, vol. 106, 1987, p. 718.

Sari, J. C. et al., "Thermodynamic study on the interaction of periplasmic-binding proteins of Eschericia coil with their substrates," 6-*General Biochem.*, Vol. 97, 1982, p. 219.

Matsuoka, H. et al., "Semiconductor biosensor modeled on a taste cell," *Chemical Abstracts*, vol. 98, 1983, p. 300.

Georgiou, G. et al., Continuous Immobilized Recombinant Protein Production from E. coli Capable of Selective Protein Excretion: A Feasibility Study, *Biotechnology Progress*, vol. 1, No. 1, Mar. 1985, pp. 75–79.

Janata, J., Electrochemistry of Chemically Sensitive Field Effect Transistors, *Sensors and Actuators*, vol. 4, No. 2 (Oct., 1983), pp. 255–265.

Ho, N. J. et al., Encapsulation of Polymeric Membrane-Based Ion-Selective Field Effect Transistors, *Sensors and Actuators*, vol. 4 (1983), pp. 413–421.

Moss, S. D. et al., Potassium Ion-Sensitive Field Effect Transistor, *Analytical Chemistry*, vol. 47, No. 13 (Nov., 1975), pp. 2238–2242.

Lian, W. J. et al., Flip-Flop Sensors: A New Class of Silicon Sensors, *Sensors and Actuators*, vol. 9 (1986), pp. 259–268.

Mitsubishi Electric Corp. (assignee), Urea Biosensor, *Chemical Abstracts*, vol. 103, 1985, p. 268.

Mitsubishi Electric Corp. (assignee), Multiple Enzyme Sensor, *Chemical Abstracts*, vol. 103, 1985, p. 268.

Lowe, C. R. et al., Diagnostic Device Incorporating A Biochemical Ligand, 9-*Biochem. Methods*, vol. 102, 1985, p. 285.

Shiro, T., Coating Resins for Biologically Active Material on Field-Effect Transistors, *Chemical Abstracts*, vol. 104, 1986, p. 316.

Liu, C. C. et al., Apparatus for Electrochemical Measurement, *Chemical Abstracts*, vol. 104, 1986, p. 316.

*Primary Examiner*—T. Tung

DIGITAL BIOSENSORS AND METHOD OF USING SAME

This application is a continuation application based on prior copending application Ser. No. 047,080, filed on May 5, 1987, now abandoned.

FIELD OF THE INVENTION

This invention relates to measuring systems employing sensors and, more particularly, to measuring systems employing sensors to monitor a select component of a medium.

BACKGROUND OF THE INVENTION

It is often desirable to monitor particular characteristics of a certain component of interest found in a medium. For example, the monitoring of phosphate levels in sewage is useful to determine whether the sewage has been adequately treated. Similarly, in virtually any chemical processing system, knowledge of the concentration of a particular component in solution can be useful for system control. Further, in biomedical applications, information concerning the concentration of certain components in body fluids such as blood can be extremely important to the proper diagnosis of a patient's condition.

Given the diversity of characteristics, components, and media that may be involved, a system, including a measuring instrument and a sensor, that is able to accurately produce measurements under these different conditions is subject to numerous design constraints. For example, the system may be required to provide a selective response to a particular characteristic and component of the media. The system may also be called upon to automatically respond to changes in the characteristic of the component, providing updated information with minimal operator intervention. In certain applications, the system sensor preferably would have a relatively long life and be reuseable without adverse effect upon its accuracy. Alternatively, it may be desirable in some instances to employ a sensor that is disposable. Finally, it would be desirable to produce a system that is either precalibrated, or requires no calibration, and whose size, complexity and cost are kept to a minimum.

SUMMARY OF THE INVENTION

In accordance with this invention, a system is provided for detecting a characteristic of a component of a medium. The system includes a sensor having a detector that responds electronically when exposed to the component and a binding element for binding the component to the detector. The instrument also includes a processor that is coupled to the sensor and produces an output indicative of the characteristic of the component of the medium.

In a preferred arrangement, the binding element reversibly binds the component to the detector, the medium is a solution and the characteristic of interest is the component's concentration in the solution. The binding element is an organic or inorganic ligand binder.

In accordance with a particular aspect of the invention, the detector is a semiconducting material comprising an insulated gate field-effect transistor. The transistor has a gate insulator region, source region and drain region. The organic or inorganic ligand binder is coupled to the gate insulator region, while the processor applies an electronic signal between the source region and drain region of the transistor. The binding of the component to the gate insulator region influences the signal and the processor responds by producing an output indicative of the characteristic of the component.

In accordance with a further aspect of the invention, a plurality of insulated gate field-effect transistors are employed, with a separate organic or inorganic ligand binder being coupled to the gate region of each transistor. The separate organic or inorganic ligand binders may bind the same components and have the same or different binding coefficients, or may bind different components.

In accordance with another aspect of this invention, a method of detecting a characteristic of interest of a component of a medium is provided. The method includes the step of binding the component to a semiconducting element that responds electronically to the component. Then, the electronic response of the semiconducting element is monitored and an output indicative of the characteristic of interest is produced, the output being a function of the electronic response monitored.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT OF THE INVENTION

Figure 1:
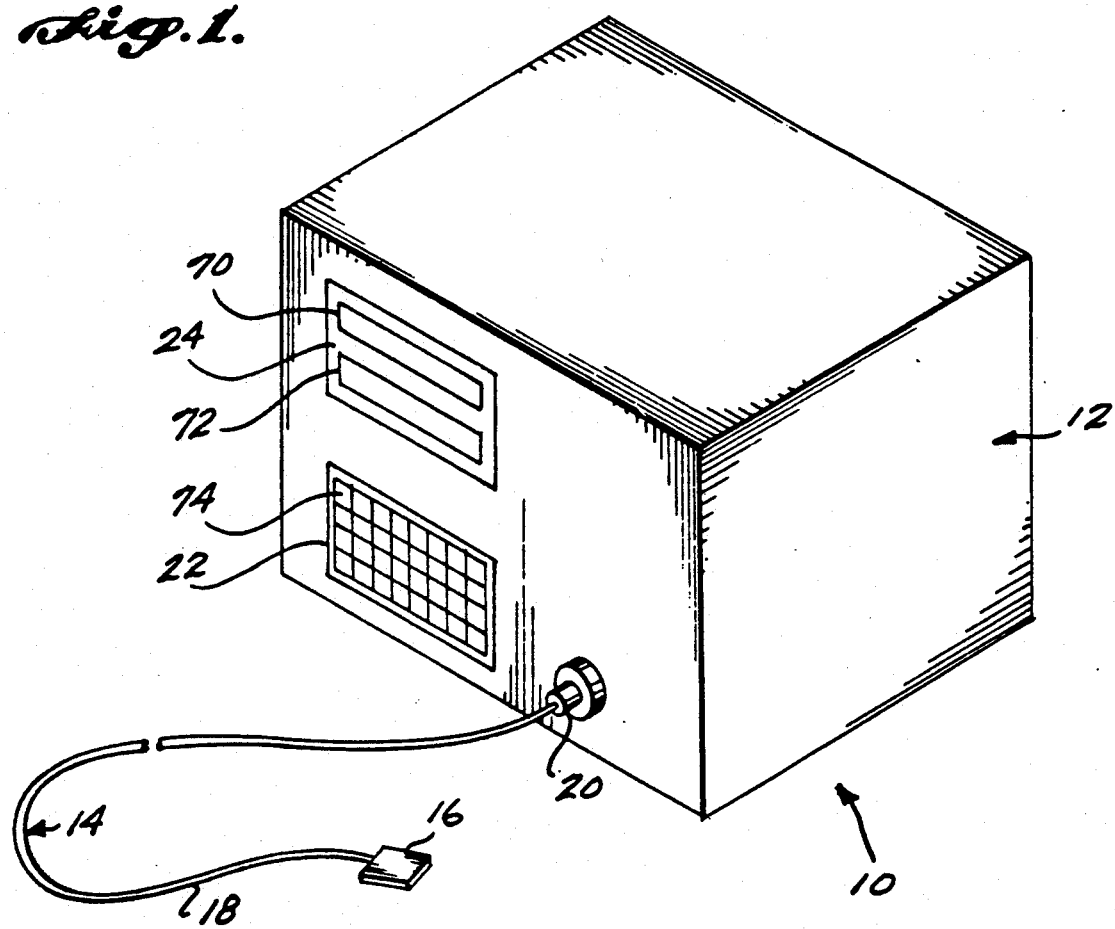
FIG. 1 is a pictorial view of a measuring system constructed in accordance with this invention, including a sensor, detachably connected to a console that controls the sensor and responds to information received from the sensor.

Referring now to FIG. 1, a measuring system 10 constructed in accordance with this invention is illustrated. As shown, measuring system 10 includes an instrument console 12 and a detachable sensor assembly 14. The distal portion of sensor assembly 14 includes a sensor element 16, which is exposed to the media containing the component of interest. The sensor element 16 is electronically and mechanically coupled to console 12 by a cable 18. A connector 20, provided at the proximal end of cable 18, allows sensor assembly 14 to be detachably connected to console 12.

The operation of sensor assembly 14 is controlled, in part, by instructions introduced through a user input such as a keypad 22 provided on the instrument console 12. The internal circuitry of console 12 monitors the particular characteristic of the component of interest by analyzing signals from sensor element 16 in the manner described in greater detail below. The resultant information is then displayed to an operator via display 24 and can also be used in a feedback control system to adjust system parameters.

Figure 2:
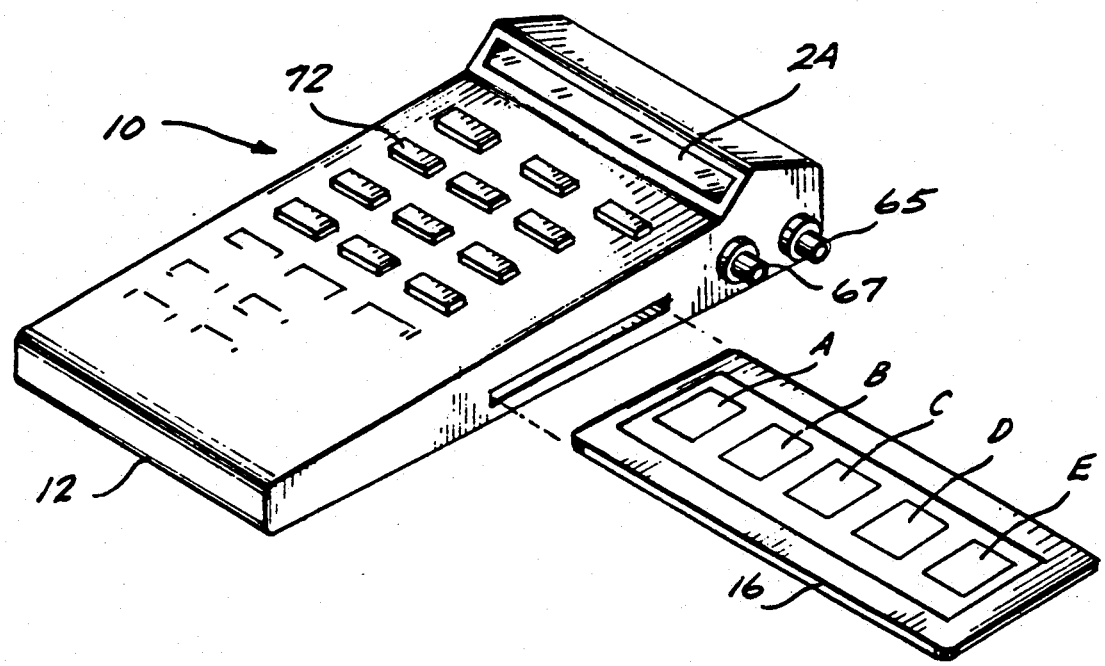
FIG. 2 is a pictorial view of an alternative embodiment of the measuring system shown in FIG. 1, including a discrete sensor.

In an alternative to the embodiment of the measuring system 10 shown in FIG. 1, the instrument console 12 is dimensioned to be handheld and is used with a discrete sensor element 16 cassette. As shown in FIG. 2, the sensor element 16 is insertable into console 12, which electrically and mechanically engages the sensor element 16 in a manner described in greater detail below.

Like the embodiment of system 10 shown in FIG. 1, the operation of the discrete sensor element 16 is controlled, in part, by instructions introduced through a user input, such as a keypad 22, provided on the instrument console 12. A particular characteristic of the component of interest is monitored via console 12 by the analysis of signals from sensor element 16, as described below. The information produced by console 12 is then displayed to the operator via a display 24.

Figure 3:
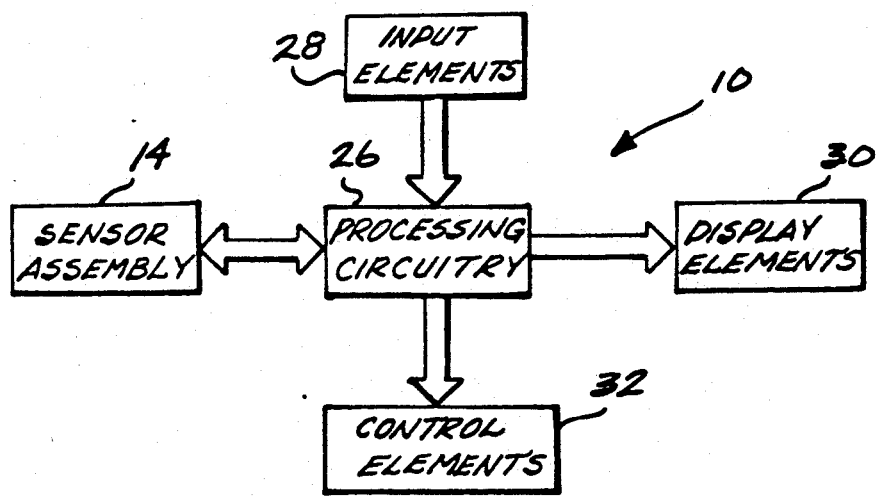
FIG. 3 is a block diagram of the measuring system illustrated in FIGS. 1 and 2.

A basic block diagram of the measuring systems 10 of FIGS. 1 and 2 is shown in FIG. 3. As shown, sensor assembly 14 is controlled by, and provides information to, the processing circuit 26 located within console 12. The operation of processing circuit 26 is controlled, in part, by operator instructions received via input elements 28. Display elements 30 convert information from processing circuit 26 into a form usable by the operator. Similarly, control elements 32 convert information about the characteristic of interest received from processing circuit 26 into forms usable by a feedback control system.

Turning now to a more detailed description of the various components of measuring system 10, the detachable sensor assembly 14 is first considered. As shown in the more detailed block diagram of system 10 provided in FIG. 4, sensor element 16 includes a binding element 32 immobilized on a semiconducting element 34. The function of binding element 32 is preferably to selectively and reversibly bind the component of interest to the semiconducting element 34 when sensor element 16 is exposed to, for example, a solution. As will be discussed in greater detail below, the binding of certain select components to the semiconducting element 34 induces a measurable response in semiconducting element 34. As a result, the concentration or activity of the component in solution, for example, can be monitored as a function of the electronic characteristics of the semiconducting element 34. The electronic response of semiconducting element 34 is applied to a conditioning circuit 36 which may also be included on sensor element 16. As described below, circuit 36 appropriately conditions the response of semiconductor element 34 for transmission to processing circuit 26 via cable 18. A binding reversal element 38 is additionally included on sensor element 16 to reverse the action of the binding element 32.

Addressing these components of sensor element 16 in greater detail, binding element 32 is preferably a biologically active molecule immobilized on the semiconducting element 34. Such biologically active molecules are selected from proteins, protein fragments and binding partners that are capable of forming reversible binding complexes with the component, which is typically a small molecule ligand. The preferred biologically active molecules are a class of proteins termed "binding proteins" that reside in the space between the inner and outer membranes (periplasmic space) of the gram-negative prokaryotes. These proteins bind their respective nutrients with high specificity and affinity. These proteins also bind their respective ligand through a broad range of pH values and ionic strengths.

It is known that protein ligand binding causes a conformational change in the protein (Ames, G. F. L., Ann. Rev. Biochemistry, 1986, 55:397-425) resulting in a tight binding complex. Binding affinities ($K_D$) for ligand binding proteins are described in Furlong, C. E., Methods in Enzymology 125: 279-289 (1986), hereby incorporated by reference. The high ligand affinity of these proteins is directly related to a low dissociation rate, requiring that these proteins be "encouraged" to release their ligand by external stimulus to prevent the sensor from remaining saturated. It has been discovered in accordance with the present invention that prokaryote periplasmic binding proteins which have formed a high affinity complex with a ligand will release the ligand upon heating (for example to temperatures above 75° C. for the phosphate-binding protein) and that the binding protein will renature to its original conformation upon cooling to ambient temperature, provided that the binding protein is immobilized on a surface prior to heating. If the protein is not immobilized, denaturing by heating causes irreversible protein coagulation. Thus, these binding proteins may be suitably employed in a sensor for detecting low concentrations (near the $K_D$) of ligands in aqueous solution and they may be cycled by heating and cooling or other reversibly denaturing conditions such as organic solvents and chaotropic agents to release the bound ligand and regenerate the active sensor.

As will be appreciated, the ligand of interest may be a charged or uncharged species. The corresponding binding protein may be selected from those described by Furlong, as referenced above. Still other proteins suitable for use include those described by Copeland, B. R. et al., J. Biol. Chem. 257 15065-15071 (1982), herein incorporated by reference.

In general, the biologically active molecule need only bind its ligand with an affinity and specificity appropriate to the particular application. A general procedure for identifying and isolating proteins is described by Copeland, B. R. et al., referenced above. The entire protein may not be necessary if an active binding domain of a protein can be isolated and if the domain can be reversibly denatured.

It is preferred that the $K_D$ of the binding protein be near the concentration of the solution being analyzed. If the concentration of ligand in solution is higher than the $K_D$ of the protein, the measuring system can employ a feedback controlled dilution system to adjust, calculate and control the necessary dilution of the original solution to bring it within measurement range for a given binding protein attached to the semiconducting element 34.

The means for immobilizing a binding component 32 on semiconducting element 34 depends on the composition of semiconducting element 34. When the binding protein is immobilized on a silicon dioxide region at the surface of semiconducting element 34, described in greater detail below, the silicon dioxide surface is preferably derivatized using vapor phase deposition of silane compounds, such as 3-aminoprophyltriethoxysilane (APTES). Vapor phase deposition in this manner deposits a chemically active layer of the silane compound covalently bonded to the SiO$_2$ surface. Alternatively, the surface can be derivatized using liquid phase deposition.

A binding protein, selected from those previously described, is then immobilized on the derivatized surface of the semiconductor by a covalent bond. Bonding the protein to the derivatized SiO$_2$ surface must be conducted under conditions that preserve the biological activity of the binding protein. Bifunctional cross-linkers, of the type disclosed in the 1986-87 catalog of the Peirce Chemical Company, Rockfork, Ill., pages 312-340, herein incorporated by reference, are suitable.

Figure 5:
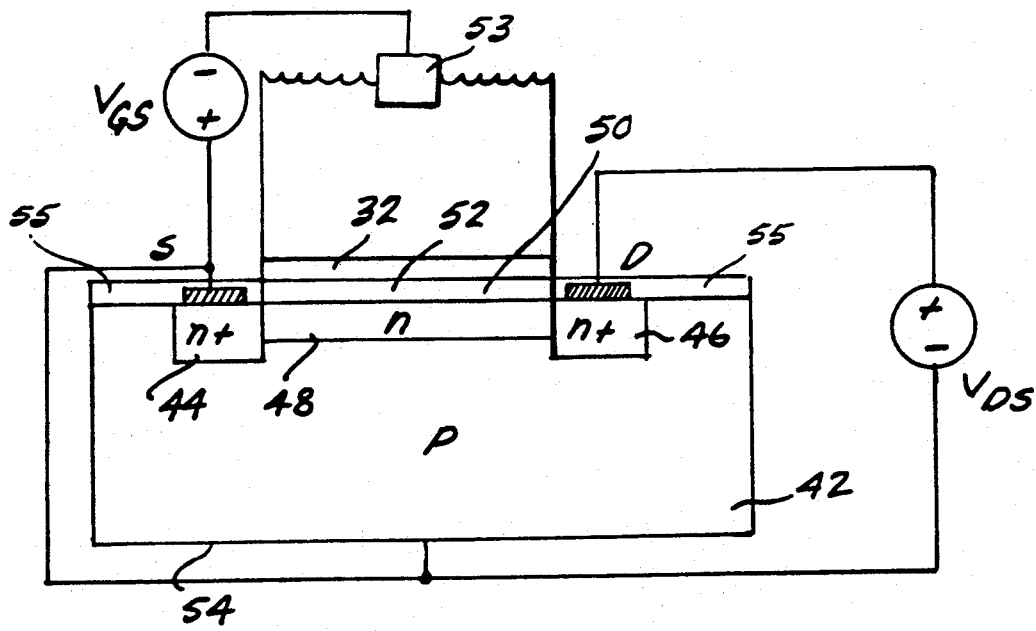
FIG. 5 is a pictorial representation of a portion of a sensor constructed in accordance with this invention.

Turning now to a more detailed description of semiconducting element 34, reference is had to FIG. 5. As shown, semiconducting element 34 is preferably configured as an insulated-gate, field-effect transistor (IGFET) 40. As noted previously, the function of semiconducting element 34 is to respond electronically to the action of binding element 32. The IGFET configuration is preferred for its extremely high input impedance, which limits the influence that semiconducting element 34 has on binding element 32.

As shown in the representation of IGFET 40 provided in FIG. 5, IGFET 40 is constructed for operation in an n-channel depletion-mode. More particularly, IGFET 40 includes a substrate 42 formed of a semiconducting material, such as silicon, that has a p-type impurity added to increase the number of positive charge carriers, or holes, present in the material. Separate source 44 and drain 46 regions are provided at spaced-apart locations on the surface of substrate 42. While the source 44 and drain 46 are also preferably made of a silicon semiconducting material, they are heavily doped with an n-type impurity that significantly increases the number of negative charge carriers, or electrons, present in the material. A channel 48 of semiconducting material extends between source 44 and drain 46 and is lightly doped with an n-type impurity to provide a relatively low conductivity. An insulative material 50, such as silicon dioxide, is deposited over channel 48 to produce the high input impedance noted above. A gate region 52 of IGFET 40 is defined by the insulating material 50 and, in this case, has the previously described binding element 32 immobilized thereon. A gate electrode 53 is spaced apart from the gate region 52 and allows a reference voltage to be applied to the gate region 52. Ohmic contacts 54 allow the substrate 42, source 44 and drain 46 regions of IGFET 40 to be connected to external circuitry, while the remainder is insulated by dielectric material 55.

Operation of IGFET 40 is basically as follows. With the source 44 and substrate 42 electronically connected and no voltage applied to the gate insulator 50 via reference electrode 53, the application of a small positive voltage $V_{DS}$ between the drain 46 and source 44 establishes a reverse-bias across the p-n junction. The reverse bias forms a depletion region between the channel 48 and substrate 42 that effectively isolates the two regions. With IGFET 40 operated in this manner, current flows from source 44 to drain 46 through the channel 48, which acts as a resistor whose resistance depends on the physical construction of channel 48.

Now, assume that binding element 32 has been constructed to selectively bind a negatively charged component in solution to gate insulator 50. The resultant negative potential, which may be supplemented by an external gate-to-source voltage via electrode 53, produces a field at the insulative material 50 that repels electrons in the n-type material of channel 48. As a result, the conductivity of channel 48 decreases and, at some point, Vp, the magnitude of the gate-to-source voltage $V_{GS}$ may become sufficiently large to effectively "pinch off" channel 48, preventing the flow of drain current $I_D$. Below pinch-off and for relatively low drain-to-source voltages $V_{DS}$ (less than $V_{GS}-V_p$), IGFET 40 effectively acts as a voltage-controlled linear resistance, with the gate potential produced by the operation of binding element 32 and any external source controlling resistance. For larger values of $V_{DS}$, however, the drain current $I_D$ varies only with $V_{GS}$ and is not a function of $V_{DS}$.

As will be appreciated, an IGFET 40 constructed in the foregoing manner can be used to detect the concentration of the component in solution in the following manner. With the appropriate binding element 32 immobilized upon insulative material 50 and some reference to the substrate 42 provided, $V_{GS}$ is a function of the number of negatively charged components bound to insulative material 50. With a constant voltage $V_{DS}$ applied from processing circuit 26, the drain current $I_D$ is inversely proportional to the magnitude of $V_{GS}$ and, hence, the concentration of the negatively charged component in solution.

Although semiconducting element 34 has been described as an n-channel, depletion-mode IGFET constructed of silicon with a silicon dioxide insulative layer, various other configurations could be employed. For example, IGFET 40 could be constructed for use with a p-type channel as well as for use in an enhancement-mode. Alternative semiconducting materials that can be used in IGFET 40 include Ge, SiC, silicon-on-sapphire and GaAs, while other usable insulating materials include Si$_3$N$_4$, Al$_2$O$_3$, tantalum oxide, and titanium oxide. Alternatively, those skilled in the art will appreciate that certain metals such as aluminum, antimony, chrome, gold, platinum, silver and metal/metal oxide systems of these metals can be used to construct metal and/or metal oxide electrodes which could be employed to measure conductance, resistance or potentiometric changes in response to the operation of the binding element 32 in solution. Further, it is contemplated that constructions employing junction field-effect transistors, bipolar transistors, gate-controlled diodes, capacitors, charge coupled devices, diodes, and unijunction transistors could be employed, with the charge generation, charge redistribution, change in dipole moment, change in conductivity, or change in capacitance caused by the operation of binding element 32 upon the component in solution producing an electronic response that can be correlated to, for example, the concentration of the component.

Figure 4:
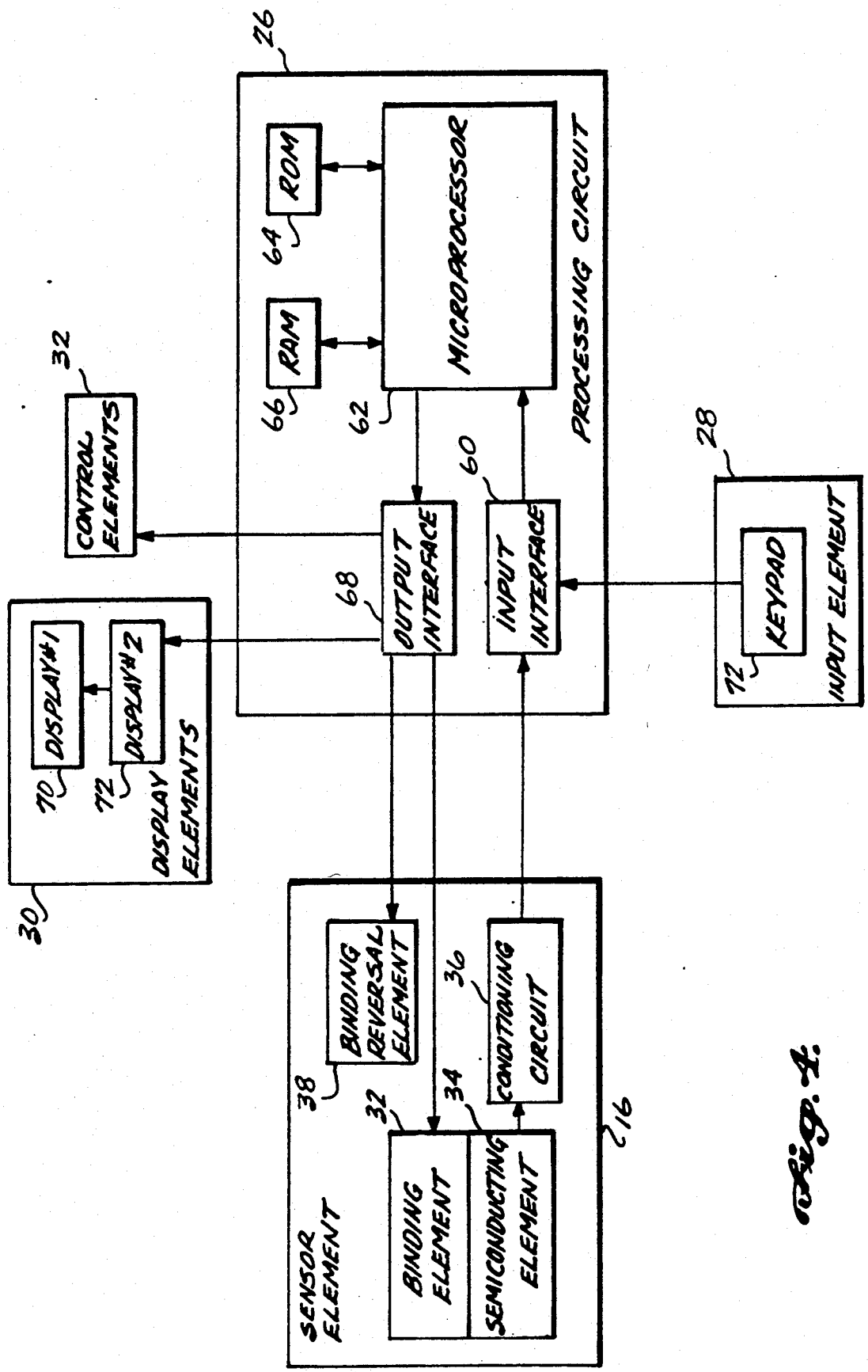
FIG. 4 is a more detailed block diagram of the measuring system illustrated in FIG. 3.

In the particular IGFET 40 construction represented in FIG. 4, IGFET 40 preferably has a gate region 52 whose dimensions are on the order of 10 microns by 200 microns and a substrate resistivity of six to ten ohms-centimeter. The depth of the silicon dioxide insulative layer 50 is approximately 500 to 1000 Å and has a surface area corresponding to that of gate region 52.

With the binding proteins 32 immobilized on the insulative material 50 in the manner described above, a protein density per square centimeter of gate insulator region 52 of approximately 10$^{13}$ can be achieved. In this manner, when a protein 32 having a K$_D$ of one is employed, and the proteins 32 have completed their binding of the component to the insulative material 50, the resultant charge at the gate or gate insulator 52 produces a voltage sensitivity when referenced to the substrate that is on the order of the Nernstian Response (60 mV/decade/equivalent charge).

Turning now to a more detailed description of the conditioning circuit 36 illustrated in FIG. 4, the function of conditioning circuit 36 is to condition the electronic response of IGFET 40 to the action of binding protein 32, so that the response is more easily received and analyzed by processing circuit 26. Because of the relatively small variations in the charge or other electronic signal produced at the gate insulator 50 by the operation of binding protein 32, conditioning circuit 36 must be responsive to relatively slight input variations. Further, because information in digital form is frequently more easily stored and processed by subsequent circuitry, conditioning circuit 36 preferably converts the response of IGFET(s) 40 into digital form.

Figure 6:
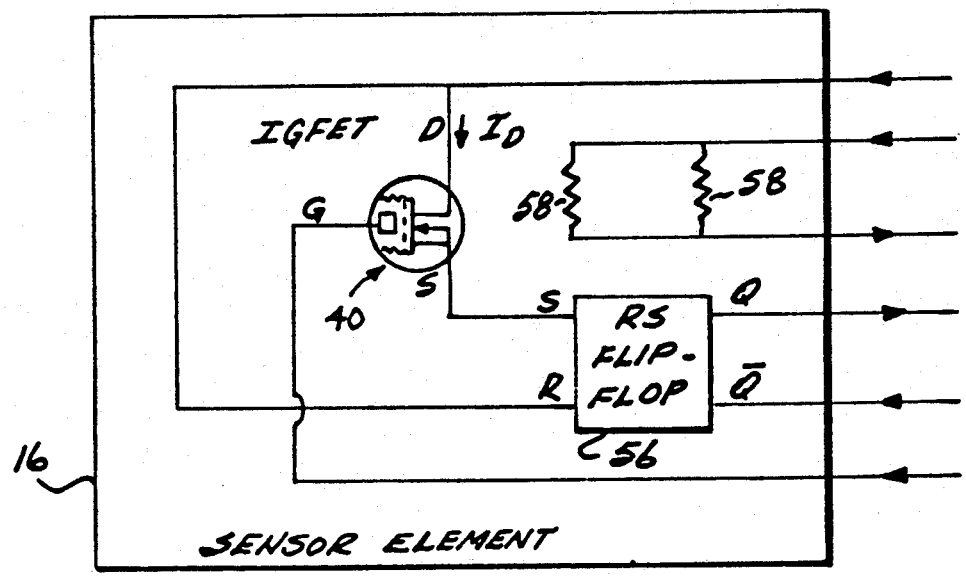
FIG. 6 is a schematic representation of the sensor represented in FIG. 4.

In light of the foregoing observations, the use of unstably operated flip-flops in conditioning circuit 36, as briefly described below, is preferred. Additional detail concerning flip-flops operated in this manner is provided by D. Lian and S. Middelhoek in Flip-Flop Sensors: A New Class Of Silicon Sensors, 9 *Sensors and Actuators*, 259–268 (1986). As shown in FIG. 6, at least one flip-flop 56 is employed. Flip-flop 56 may be of the reset-set type commonly designated RS and constructed, for example, with two cross-coupled NOR gates having inputs designated R and S and producing outputs designated Q and $\bar{Q}$.

Basically, the flip-flop 56 has two stable states. In one stable state, the Q output is high and the $\bar{Q}$ output is low. In the other stable state, the $\bar{Q}$ output is high and the Q output low. If an abrupt voltage pulse is applied to the S input of flip-flop 56, flip-flop 56 is brought into an unstable state. With the flip-flop 56 in this unstable state, it is highly sensitive to remaining or injected charges, asymmetries in the NOR gates, noise, and input signals.

Without the influence of input signals, the probability that the flip-flop 56 will transfer to one or the other of the stable states can be determined statistically. Then, with the IGFET 40 connected to the S input of flip-flop 56, even an extremely low signal variation from IGFET 40 will have an easily measured effect on the probability of a particular stable state of flip-flop 56 occurring. More particularly, the number of ones produced at output Q, for example, can be counted over a period during which the flip-flop 56 is repeatedly brought into an unstable state at a high frequency. The ratio between the number of high outputs at the Q output to the number of unstable states can then be used to indicate the response of IGFET 40 to the operation of binding element 32. As a result, accuracy is enhanced both by the sensitivity of each individual measurement produced in this manner and the ability to repeat that measurement a relatively large number of times within a short time frame.

The foregoing operation of IGFET 40 and flip-flop 56 can perhaps be more readily understood in connection with the diagram provided in FIG. 6. As shown, IGFET 40 is connected with its drain 46 and source 44 in series with the S input of flip-flop 56. A voltage pulse from processing circuit 26 is then applied to the drain 46 of IGFET 40 and input R of flip-flop 56, which are electronically connected. As will be appreciated from the preceding discussion, the imbalance produced by the IGFET 40 as a result of the operation of binding element 32 effects the probability of either the Q or $\bar{Q}$ output being high. These outputs are continuously monitored by processing circuit 26, which then compares them with the number of voltage pulses applied to sensor element 16 to determine the concentration of the component in solution. As will be appreciated, the comparison between outputs and voltage pulses may vary directly or inversely in proportion to the concentration being determined depending upon the particular configuration of the IGFET 40 employed, the binding protein 32 selected, and the charge of the component of interest.

Given the time delays involved in the logic elements employed in flip-flop 56, it may be desirable to control flip-flop operation through a clock input designated $C_C$. Further, the details of flip-flop 56 can be varied and J-K flip-flops, D flip-flops and master-slave flip-flops, for example, can be employed in place of the RS flip-flop illustrated. Regardless of the construction of flip-flop 56, however, it is preferably a solid-state device integrated with the IGFET 40 onto a single substrate. As is discussed in greater detail below, a plurality of such combined IGFETs 40 and flip-flops 56 can be used to provide a continuum of responses to a particular characteristic of a component in solution or to respond to various components, depending on the particular binding elements 32 selected.

The final section of sensor element 16 to be discussed is the binding reversal element 38. As suggested above, the particular binding element 32 selected can be induced to release the component bound to the insulative material 50 by increasing the temperature of the gate 52 to approximately 75° C. To produce the required temperature change, diffused or thin-film resistors 58 can be integrated with the other components or the sensor element 16. The number, location, and resistivity of resistors 58, as well as the voltage applied, determines their power loss and, hence, the heat transferred to sensor element 16.

While thermal binding reversal can also be achieved by the immersion of sensor element 16 in water of a sufficiently high temperature, or through the use of denaturing agents, the use of resistors 58 allows the release of components to be effected in situ under the automatic control of processing circuit 26. As will be discussed in greater detail below, this feature has numerous advantages when employed in automatic control circuitry. To enhance the efficiency of the reversal performed by resistors 58, or to allow a more complete reversal at lower temperature, the charge at the surface of gate 52 may also be reversed.

As will be appreciated, and as is discussed in greater detail below, sensor element 16 may include a plurality of IGFETs 40 and flip-flops 56. The insulative material 50 of each IGFET 40 may have the same or different binding elements 32 immobilized thereon and the binding coefficients $K_D$ of the various immobilized binding elements 32 may be the same or different, as desired. For the purpose of illustration, the discussions of system 10 operation below will treat the sensor element 16 shown in FIG. 1 as including a single IGFET 40, while the sensor element 16 depicted in FIGS. 2 and 7 will be considered as having five separate IGFET 40 and flip-flop 56 sections schematically designated A, B, C, D, and E.

Turning now to a more detailed discussion of the processing circuit 26 shown in FIG. 3, reference is again had to FIG. 4. As shown, information received from sensor element 16 is conditioned by an input interface 60 for transmission to a microprocessor 62. As noted previously, with the use of flip-flop 56, this information includes high and low flip-flop outputs produced in response to the voltage pulses applied by microprocessor 62 to the drain 46 of IGFET 40 and the S input of flip-flop 56 in accordance with program instructions stored in read-only memory (ROM) 64. A random-access memory (RAM) 66 stores the number of voltage pulses applied by microprocessor 62 to the sensor element 16 during a predetermined time interval, allowing microprocessor 62 to compute the percentage of times that a particular stable state of flip-flop 56 is achieved during that interval.

In accordance with further instructions stored in ROM 64, microprocessor 62 compares this percentage with data representing an empirically derived calibration curve, also stored in ROM 64. The calibration curve is basically a plot of independently determined information correlating, for example, various percentages of high flip-flop 56 output states and the corresponding component concentrations. Thus, by referring to the data in ROM 64, microprocessor 62 is able to determine the concentration of the component of interest in solution.

An output interface 68 provides the information concerning concentration to the display elements 30. In the embodiment shown in FIG. 1, the physical display 24 includes an alphanumeric display 70, such as a light-emitting diode (LED) array or liquid crystal display (LCD), that provides a representation of the concentration. A second alphanumeric display 72 indicates whether some threshold change in concentration has been monitored over a predetermined interval.

Information concerning the concentration computed by microprocessor 62 can also be applied to certain control elements 32 included as part of a larger control system. As will be appreciated, when supplied with information about the concentration of a component in solution and whether that concentration has varied by a predetermined amount over a given interval, the control elements 32 are able to initiate changes in the processing of the solution to achieve some predetermined component concentration. Thus, in addition to providing raw information to control elements 32 microprocessor 62 may instruct control elements 32 concerning the proper response to that information.

Via output interface 68, microprocessor 62 also provides energy to the binding reversal element 38 at intervals and levels determined in accordance with instructions from ROM 64. In this manner, the binding element 32 is caused to release the component back into solution as described previously in connection with the discussion of sensor element 16.

As will be appreciated, the instructions stored in ROM 64 that govern microprocessor 62 operation can be entered or altered by the operator's use of input elements 28. These elements 28 include a keypad 72 such as pressure-sensitive switches 74 that allow, for example, binding reversal to be initiated manually or automatically at predetermined intervals. Further, keyboard 72 allows the instrument console to be turned on and information entered into RAM 66 for use by microprocessor 62 in controlling the operation of measuring system 10.

Summarizing the operation of the measuring systems 10 described above, with respect to the system 10 shown in FIG. 1, the sensor element 16 is exposed to a solution of interest at some location remote from console 12. The binding protein 32, which is receptive to a particular component of the solution and has a predetermined binding coefficient $K_D$, is provided on the gate insulator region 52 of IGFET 40. As the binding protein 32 couples the component in solution to the insulative material 50 of IGFET 40, the drain current established in IGFET 40 by processing circuit 26, via cable 18, varies as a function of, for example, the concentration of the component in solution. With IGFET 40 connected in series with one of the inputs of the flip-flop 56, an imbalance in the unstable operation of flip-flop 56 results. The microprocessor 62 monitors this imbalance via signals received through cable 18 and determines the concentration of the component in solution by referring to empirically derived calibration curves stored in ROM 64. Microprocessor 62 provides the appropriate output information to the user via the display elements 32 and offers control over a solution processing system via control elements 32. The sensor element 16 can then be effectively "cleared" by activating the binding reversal element 38, causing binding element 32 to release the component of interest.

In the arrangement shown in FIG. 2, the sensor element 16 includes five separate IGFET 40 and flip-flop 56 sections designated A, B, C, D, and E. While the sensor element 16 may be exposed to the solution of interest at some location remote from console 12 and subsequently analyzed upon insertion into console 12, in a preferred arrangement the sensor element 16 is both exposed to the solution and analyzed by processing circuit 26 after insertion. In this regard, the mechanical engagement between console 12 and sensor element 16 provides a fluid tight seal around sensor element 16. A first port 65 provided on the console 12 allows the solution of interest to be introduced into console 12, exposing the binding elements 32 on sensor element 16. An exit port 67 then exhausts the solution from console 12.

As will be appreciated, regardless of the manner in which the sensor element 16 of FIG. 2 is exposed to the solution of interest, sensor element 16 is electronically connected to the processing circuit 26 upon insertion into console 12. Processing circuit 26 controls and responds to information from each section A, B, C, D, and E in substantially the same manner described above for the single IGFET 40 and flip-flop 56 arrangement. Keypad 72 and display 24 allow operator inputs and information outputs, respectively, to be effected.

As will be appreciated, numerous variations of the multiple IGFET 40 and flip-flop 56 sensor element 16 can be employed to adapt measuring system 10 for use in particular applications. If the same binding element 32 having the same binding coefficient or affinity $K_D$ is provided on the gate insulator region 52 of each IGFET 40, information from each IGFET 40 and flip-flop 56 can be used to simultaneously determine the concentration of the component in solution and produce an average value for display. Alternatively, this configuration allows information to be extracted from certain IGFETs 40, while the operation of the binding elements 32 on other IGFET 40 gates 52 is reversed. For example, with the sensor element 16 shown in FIGS. 2 and 7 employed, the operation of the binding elements 32 on the IGFETs 40 in section A can be reversed while information is extracted from sections B, C, D, and E. Then the operation of sections B, C, D, and E can be reversed sequentially while information is extracted from the other nonreversed sections. Although this technique requires some thermal isolation between adjacent IGFETs 40, it provides the possibility of maintaining continuous, updated, measurements of the component concentration in solution, with some IGFETs 40 always collecting information. As will be appreciated, this energization and reversal process is controlled by microprocessor 62 in response to instructions stored in ROM 64.

In another embodiment of sensor element 16 employing multiple IGFETs 40 and flip-flops 56, different binding elements 32 may be attached to the gates or gate insulators 52 of different IGFETs 40. If these binding elements 32 are selected to respond to different components in the solution, it is then possible for microprocessor 62 to analyze characteristics of different components of the solution simultaneously. For example, with the sensor element 16 shown in FIGS. 2 and 7 constructed to operate in this manner, the binding elements 32 immobilized on the insulating material 50 of the IGFETs 40 in each section A, B, C, D, and E allow section A to respond to a first component, section B to respond to a second component, section C to respond to a third component and so on. By employing a plurality of IGFETs 40 with each binding protein 32 selected, it is further possible to provide the continuous analysis described above for each component.

In another embodiment of the multiple IGFET 40 and flip-flop 56 sensor element 16, binding elements 32 for the same components are immobilized upon the insulative material 50 of each IGFET 40 but the binding coefficient $K_D$ is different for each of the binding elements 32. As will be appreciated, when a sensor element 16 constructed in this manner is exposed to a solution containing the component of interest, the degree to which the component is bound to the gate region 52 of a particular IGFET 40 will be a function of the binding coefficient $K_D$ associated with the corresponding binding element 32. Thus, a series of incremental responses will be received by microprocessor 62 from the various IGFETs 40 and flip-flops 56.

Figure 7:
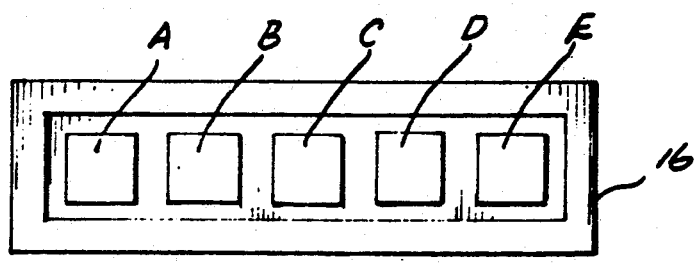
FIG. 7 is a pictorial representation of a sensor, constructed in accordance with this invention, having a plurality of sensing regions; and, FIG. 8 is a graphical illustration of the response of a particular sensor, constructed in accordance with this invention, to the changing concentration of a component in solution.
Figure 8:
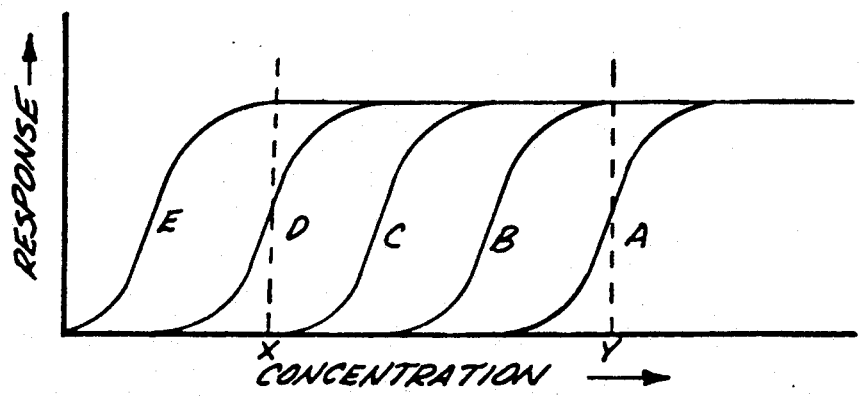

Addressing this arrangement in greater detail, with the sensor element 16 shown in FIGS. 2 and 7 constructed in this manner, the five sensor sections A, B, C, D, and E each include at least one IGFET 40. If the binding coefficient $K_D$ of the binding proteins 32 immobilized on the insulative material 50 of the IGFETs 40 decreases with each consecutive section A, B, C, D, and E, the magnitude of the response of the IGFETs 40 in each section to changing component concentration will be as shown in FIG. 8. While the curves shown are sigmoidal, the usual response vs. concentration curves are hyperbolic in nature. As indicated, the magnitude of the response at each section includes a relatively linear region during which an increase in concentration causes a corresponding increase in the magnitude of the section's response. Beyond this linear region, however, a saturated region exists in which increasing concentration of the component in solution does not substantially affect the magnitude of the section's response.

As will be appreciated, the response of an IGFET 40 in any particular section is determined by monitoring the drain current $I_D$. With flip-flops 56 employed, this becomes a matter of comparing the number of high outputs received with the number of voltage pulses applied to IGFET 40. Alternatively, the analog value of the drain current $I_D$ can be measured directly by processing circuit 26. While $I_D$ is actually inversely proportional to concentration in the linear region of each section's response, the following discussion, as well as FIG. 8, treats the magnitude of the various sections' response positively for convenience.

Whether the response of sensor section A, B, C, D, and E is produced via digital or analog hardware, the resultant information can be analyzed in several fashions. First, a "digital" mode of analysis will be addressed. In this mode of operation, microprocessor 62 receives appropriately conditioned information concerning the response of each sensor section A, B, C, D, and E. With reference to FIG. 8, if sensor element 16 is exposed to a solution having a component concentration designated X, the response of section E will fall within the saturated region and the section D response will be within the linear region. The remaining sections A, B, and C will be relatively unaffected. By requiring that the response of a section reach some predetermined threshold close to saturation before an output is produced, microprocessor 62 will only produce a high output for section E.

Now, if the concentration of the component in solution is increased to Y, the operation of sections B, C, D, and E will all be within the saturated region and only section A will be operating in the linear region. As a result, microprocessor 62 will produce high outputs corresponding to sections B, C, D, and E of sensor element 16.

In this manner an effectively digital analysis of the response of sensor element 16 is achieved. More particularly, if a high output corresponding only to the operation of section E is produced, a relatively low concentration is indicated. If high outputs for sections D and C are also produced, an intermediate concentration is indicated. When sensor element 16 is exposed to a solution including the component of interest in relatively high concentration, high outputs for all five sections will result.

Thus, by appropriately selecting the binding coefficient $K_D$ of the various binding elements 32, as well as the number of sections and relative variation between the various binding elements 32, substantially any quantization of the sensor element response can be achieved. Further, with a sufficiently large number of IGFETs 40 employed, certain error desensitization techniques can be employed. More particularly, if sensor element 16 included thirty sections and the response of section ten through thirty was high, with the exception of section twenty-seven, microprocessor 62 could be instructed to reject the output of section twenty-seven as being most likely erroneous. As will be appreciated, with a single section employed such a correction would not be possible.

Because the accuracy of this digital operation is a function, in part, of the number of sections employed, if the sensor element 16 only includes a few sections it may be desirable to enhance the accuracy of the resultant measurement by switching microprocessor 62 to an "analog" mode of analysis. In this mode of operation, if the concentration of the component in solution is, for example, X, as shown in FIG. 8, microprocessor 62 can use the information from section D to determine the corresponding concentration by referring to empirically derived calibration curves stored in ROM 64. Thus, even though the response of section D might be inadequate to initiate a digital output from microprocessor 62, in the analog mode of operation, valuable information is obtained enhancing accuracy.

Regardless of the operation of sensor element 16, a system 10 constructed in accordance with this invention does not require the use of external standard calibration references. More particularly, given the precise nature of the $K_D$ of the binding elements 32, the relationship between the output of sensor element 16 and the concentration of the component in solution does not require adjustment between sensors.

As will be appreciated, a measuring system 10 constructed in the preceding manner has numerous applications. In the medical industry, system 10 can be used for blood and urine analysis. One specific example of a digital detector employs monoclonal antibodies directed against a drug. The binding constants of the monoclonal antibodies are determined by equilibrium dialysis. Antibodies with the appropriate affinities are used to construct a detector that covers the entire range of drug levels found in physiological fluids. In various industries, including the food industry, system 10 can be used for process monitoring and system/quality control. In agriculture, soil and fertilizer analysis can be performed by system 10. The monitoring and management of waste streams provides an environmental application for system 10.

Those skilled in the art will recognize that the embodiments disclosed herein are exemplary in nature and that various changes can be made therein without departing from the scope and spirit of the invention. In this regard, and as was previously mentioned, the invention is readily embodied with various semiconductor configurations. Further, the information produced can be analyzed in either analog or digital form. Thus, an analog-to-digital converter could be employed in place of the flip-flops described or the analog output of the IGFET could be analyzed directly. Numerous configurations of the sensor can also be provided to enhance the utility of the measuring instrument with respect to a particular application. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A sensor for detecting a characteristic of a component of a medium comprising:
   a plurality of field-effect transistors for responding electronically when exposed to said component; and
   organic ligand binders for binding said component to said field-effect transistors, a separate said organic ligand binder being coupled to each said field-effect transistor, each said separate organic ligand binder having a different binding coefficient with respect to said component of said solution.

2. A system for detecting a characteristic of a component of a medium, said system comprising:
   a sensor including detection means for responding electronically when exposed to said component and a plurality of binding means for binding said component to said detection means, said detection means including a plurality of detection elements, upon which said binding means are immobilized, said binding means being immobilized on at least two separate said detection elements binding the same component of said medium but having different binding coefficients, each said detection element producing an electronic response to the binding of said component to said detection element by said binding means immobilized thereon; and
   processing means, coupled to said sensor, for producing an output indicative of said characteristic of said component of said medium.

3. The system of claim 2, wherein said binding means reversibly bind said component to said detection means.

4. The system of claim 2, wherein said electronic response produced by each said detection element is an analog signal, said processing means producing a separate digital detection element signal when each said analog signal has exceeded some threshold.

5. The system of claim 4, wherein said processing means uses said digital detection element signals to produce said output indicative of said characteristic of said component.

6. The system of claim 5, wherein said processing means determines whether said digital detection element signals are in error and does not use said digital detection element signals that are determined to be in error to produce said output.

7. The system of claim 5, wherein said processing means further uses one analog signal to produce said output indicative of said characteristic of said component.

8. The system of claim 7, wherein said processing means uses the analog signal having the highest magnitude that is still less than the threshold at which said processing means produces a digital detection element signal.

9. A method of detecting a characteristic of a component of a medium, said method comprising the steps of:
   binding said component to a plurality of detection elements that respond electronically to said component, said component being bound to different said detection elements in different degrees;
   monitoring the electronic response of said detection elements to said component; and
   producing an output indicative of said characteristic of interest, said output being a function of the electronic response monitored.

10. The method of claim 9, wherein said step of binding said component to said detection elements comprises the step of reversibly binding said component to said detection elements.

11. The method of claim 10, wherein said step of producing an output indicative of said characteristic of said component further comprises the step of producing a digital output for each said detection element as a function of the electronic response of said detection element to the binding of said component.

12. The method of claim 11, further comprising the steps of determining whether any of said digital outputs are in error and rejecting said digital outputs determined to be in error.

13. A system for detecting a characteristic of a component of a medium, said system comprising:
   a sensor including a plurality of detection elements for responding electronically when exposed to said component and a plurality of binding means for binding said component to said detection elements, each said binding means being selectively responsive to a specific range of said component characteristic and being immobilized on separate said detection elements, each said detection element responding electronically to the binding of said component to said detection element; and
   processing means coupled to said sensor, for producing a digital output corresponding to the electronic response of each said detection element and analyzing said digital outputs to determine said characteristic of said component without reference to an external calibration standard.

* * * * *

UNITED STATES PATENT AND TRADEMARK OFFICE
CERTIFICATE OF CORRECTION

PATENT NO. : 5,074,977
DATED : December 24, 1991
INVENTOR(S) : Peter W. Cheung et al.

It is certified that error appears in the above-identified patent and that said Letters Patent is hereby corrected as shown below:

|  | COLUMN | LINE |  |
|---|---|---|---|
|  | 7 | 32 | "Q" should read --$\overline{Q}$-- (second occurrence); |
|  | 7 | 33 | "Q" should read --$\overline{Q}$-- (second occurrence); |
|  | 8 | 1 | "Q" should read --$\overline{Q}$--;(second Occurrence); |
| (Title Page) | [57] Abstract | 2 | "mearsuring" should read --measuring--; and |
|  | [56] References Cited | 3 | "4,020,830 5/1977 Johnson et al." should read --B1/4,020,830 9/1984 Johnson et al.--. |

Signed and Sealed this

Twenty-fifth Day of May, 1993

Attest:

MICHAEL K. KIRK

*Attesting Officer*     Acting Commissioner of Patents and Trademarks